United States Patent
Anzenberger et al.

(10) Patent No.: US 10,758,929 B2
(45) Date of Patent: Sep. 1, 2020

(54) AEROSOL GENERATOR AND AEROSOL DELIVERY DEVICE COMPRISING THE AEROSOL GENERATOR

(71) Applicant: PARI Pharma GmbH, Starnberg (DE)

(72) Inventors: Hans-Lukas Anzenberger, Munich (DE); Carola Fuchs, Neuried (DE); Thomas Gallem, München (DE); Uwe Hetzer, München (DE); Philipp Holzmann, München (DE); Gerhard Pumm, Oberau (DE)

(73) Assignee: PARI Pharma GmbH, Starnberg (DE)

( * ) Notice: Subject to any disclaimer, the term of this patent is extended or adjusted under 35 U.S.C. 154(b) by 481 days.

(21) Appl. No.: 15/320,368

(22) PCT Filed: Jun. 18, 2015

(86) PCT No.: PCT/EP2015/063707
§ 371 (c)(1),
(2) Date: Dec. 20, 2016

(87) PCT Pub. No.: WO2015/193432
PCT Pub. Date: Dec. 23, 2015

(65) Prior Publication Data
US 2018/0178240 A1 Jun. 28, 2018

(30) Foreign Application Priority Data
Jun. 20, 2014 (EP) .................................... 14173249

(51) Int. Cl.
*B05B 17/00* (2006.01)
*A61M 11/00* (2006.01)

(52) U.S. Cl.
CPC ....... *B05B 17/0646* (2013.01); *A61M 11/005* (2013.01)

(58) Field of Classification Search
CPC ..... B05B 17/0646; B05B 17/06; B05B 17/00; B05B 17/0638; A61M 11/005; A61M 15/0085; A61M 15/0086; A61M 15/0015
See application file for complete search history.

(56) References Cited

U.S. PATENT DOCUMENTS

| | | | | |
|---|---|---|---|---|
| 4,420,706 A | * | 12/1983 | Siebold | H01L 41/053 310/322 |
| 4,550,325 A | * | 10/1985 | Viola | B41J 2/14298 222/202 |
| 5,021,701 A | * | 6/1991 | Takahashi | B05B 17/0607 239/102.2 |
| 5,306,981 A | * | 4/1994 | Martel | B06B 1/06 310/323.18 |

(Continued)

FOREIGN PATENT DOCUMENTS

DE 10 2005 006 375 A1 8/2006
JP H02-061467 U 5/1990

(Continued)

OTHER PUBLICATIONS

WO2012043682 Machine Translation (Year: 2012).*

(Continued)

*Primary Examiner* — Arthur O. Hall
*Assistant Examiner* — Steven M Cernoch
(74) *Attorney, Agent, or Firm* — Wolf, Greenfield & Sacks, P.C.

(57) ABSTRACT

The invention relates to an aerosol generator (1), comprising a housing (20, 22), having a first holding member (24, 24', 24") and a second holding member (38), and a vibratable element (4) for generating an aerosol. The vibratable element (4) is at least partially accommodated in the housing (20, 22). The vibratable element (4) is contacted by and held between the first and second holding members (24, 24', 24"; 38). The first holding member (24, 24', 24") is less flexible than the second holding member (38). Further, the invention relates to an aerosol delivery device comprising the aerosol generator (1).

9 Claims, 6 Drawing Sheets

(56) References Cited

U.S. PATENT DOCUMENTS

| | | | | |
|---|---|---|---|---|
| 5,479,521 | A | * | 12/1995 | D'Avolio ................ H04M 1/03 310/324 |
| 6,446,880 | B1 | * | 9/2002 | Schram ............... B05B 17/0646 222/570 |
| 6,732,944 | B2 | * | 5/2004 | Litherland ........... A61M 11/005 239/102.1 |
| 6,948,491 | B2 | * | 9/2005 | Loeffler ............ A61M 15/0028 128/200.14 |
| 7,891,352 | B2 | * | 2/2011 | Gallem ................ A61M 11/005 128/200.14 |
| 9,050,425 | B2 | * | 6/2015 | Van Der Mark .... A61M 11/005 |
| 9,061,303 | B2 | * | 6/2015 | Waldner ............ A61M 15/0085 |
| 9,108,211 | B2 | * | 8/2015 | Ivri ..................... B05B 17/0646 |
| 2003/0196660 | A1 | * | 10/2003 | Haveri .............. A61M 15/0085 128/203.12 |
| 2003/0218077 | A1 | | 11/2003 | Boticki et al. |
| 2007/0121967 | A1 | | 5/2007 | Sjursen et al. |
| 2008/0308096 | A1 | * | 12/2008 | Borgschulte ......... A61M 11/005 128/200.14 |

FOREIGN PATENT DOCUMENTS

| | | |
|---|---|---|
| JP | 2003-532502 A | 11/2003 |
| JP | 2012-075578 A | 4/2012 |
| WO | WO 01/85244 A1 | 11/2001 |
| WO | WO 02/09889 A1 | 2/2002 |
| WO | WO 2011/083380 A1 | 7/2011 |
| WO | WO-2012043682 A1 * 4/2012 ............... A61L 2/22 |
| WO | WO 2014/040947 A1 | 3/2014 |

OTHER PUBLICATIONS

International Search Report and Written Opinion dated Sep. 17, 2015 in connection with International Application No. PCT/EP2015/063707.

International Preliminary Report on Patentability dated Apr. 29, 2016 in connection with International Application No. PCT/EP2015/063707.

PCT/EP2015/063707, Sep. 17, 2015, International Search Report and Written Opinion.

PCT/EP2015/063707, Apr. 29, 2016, International Preliminary Report on Patentability.

Japanese Notice of Reasons for Refusal dated Jun. 11, 2019 in connection with Japanese Application No. 2016-574131 and English translation thereof.

Chinese Office Action dated Apr. 17, 2020 in connection with Chinese Application No. 201580041605.8.

* cited by examiner

AEROSOL GENERATOR AND AEROSOL DELIVERY DEVICE COMPRISING THE AEROSOL GENERATOR

CROSS REFERENCE TO RELATED APPLICATIONS

This application is a national stage of PCT/EP2015/063707, filed Jun. 18, 2015, which claims priority to EP 14173249.5, filed Jun. 20, 2014, which are hereby incorporated by reference in their entirety.

FIELD OF THE INVENTION

The invention relates to an aerosol generator with a vibratable element for generating an aerosol and to an aerosol delivery device comprising the aerosol generator.

BACKGROUND ART

Aerosols for therapeutic purposes are generated and delivered to a desired location within a user's or patient's body with aerosol delivery devices. A fluid or liquid (i.e., medicament) to be aerosolised or nebulised is supplied to an aerosol generator of the aerosol delivery device, the fluid or liquid is aerosolised or nebulised by the aerosol generator and the resultant aerosol is supplied to the user or patient.

The fluid or liquid may be aerosolised or nebulised in the aerosol generator by a vibratable element, such as a vibratable head. The characteristics of the vibratable element of the aerosol generator are decisive for the quality of the generated aerosol and for the aerosol dosage accuracy. At the same time, the vibratable element is also generally very sensitive. A misalignment of the vibratable element may negatively affect the oscillatory or vibrating motion of the element during aerosol generation and therefore compromise the quality of the generated aerosol and the dosage accuracy.

An aerosol generator of this vibratable element type is disclosed in DE 10 2005 006 375 A1. In particular, DE 10 2005 006 375 A1 discloses an aerosol generator for inhalation therapy devices, in which an oscillatable assembly, consisting of at least a membrane and an oscillation generator, is mounted in an encapsulating means by means of a flexible passage contacting the oscillatable assembly. The flexible passage comprises two flexible sealing lips which contact the oscillatable assembly from two opposing sides thereof.

Since, in the aerosol, generator disclosed in DE 10 2005 006 375 A1, the flexible sealing lips exhibit the same degree of flexibility, there is a risk that the oscillatable assembly may move, e.g., tilt, during assembly and/or during operation of the aerosol generator. Such an undesired movement of the oscillatable assembly may adversely affect the oscillation or vibration thereof and thus impair the aerosol generation, both in terms of aerosol quality and aerosol dosage accuracy.

Hence, there remains a need for an aerosol generator which allows for a precise and reliable alignment of a vibratable element, thereby ensuring high aerosol quality and dosage accuracy.

SUMMARY OF THE INVENTION

One object of the invention is to provide an aerosol generator which enables precise and reliable alignment of a vibratable element for generating an aerosol. Further, the invention aims to provide an aerosol delivery device comprising this aerosol generator. These goals are achieved by an aerosol generator and an aerosol delivery device as described and claimed herein.

The invention provides an aerosol generator comprising a housing or casing, having a first holding member or support member and a second holding member or support member, and a vibratable or oscillatable element, such as a vibratable or oscillatable head, for generating an aerosol. The vibratable element is at least partially accommodated or received in the housing. The vibratable element is contacted, e.g., touched or abutted, by the first and second holding or support members and held between the first and second holding or support members. The first holding or support member is less flexible, elastic and/or resilient than the second holding or support member.

The first holding member has a lower degree of flexibility, elasticity and/or resilience than the second holding member. The first holding member is thus more rigid and/or stiff than the second holding member.

Hence, the first holding member can serve as a support, bearing, rest or abutment for supporting the vibratable element in a stable and reliable manner during assembly and operation of the aerosol generator. In this way, the alignment or orientation of the vibratable element relative to the housing can be precisely controlled during assembly of the aerosol generator, e.g., by resting the element on the first holding member, and reliably maintained throughout the assembly process and during operation of the aerosol generator. In this way, a high aerosol quality and a high aerosol dosage accuracy can be achieved.

The vibratable element may be held, i.e., held in its position relative to the housing, by the first and second holding members, in particular, held by the first holding member from a first side of the element and held by the second holding member from a second side of the element. The first side may be opposite to the second side.

The first holding member may be disposed or arranged substantially below the second holding member in operation of the aerosol generator, i.e., when the aerosol generator is held in its operational position, or vice versa. The first holding member may be disposed or arranged substantially below the vibratable element and the second holding member may be disposed or arranged substantially above the vibratable element in operation of the aerosol generator, i.e., when the aerosol generator is held in its operational position, or vice versa.

The vibratable element may be pressed or pushed by the first holding member and/or the second holding member. The vibratable element may be pressed or pushed by the second holding member against the first holding member, e.g., by an elastic force, resilient force or spring force of the second holding member.

The first holding member and/or the second holding member may be configured to hold the vibratable element in its position relative to the housing in one, two or more directions, e.g., in two directions which are orthogonal or perpendicular to each other. In this way, the positioning accuracy of the vibratable element in the housing can be further improved.

The first holding member may be substantially rigid. In this way, a particularly high degree of positioning accuracy of the vibratable element in, i.e., relative to, the housing can be achieved. Further, it has been found by the present inventors that a substantially rigid first holding member does not adversely affect the vibration or oscillation behaviour or characteristics of the vibratable element.

The first holding member may be made of a substantially rigid material, such as hard plastic, glass fibre, crystal ball, metal, ceramic, colour pigmentation, as well as a combination thereof, like blue or green polypropylene with 20% crystal ball fraction (e.g. Piolen® P GK20A110), or the like. The substantially rigid material of the first holding member reduces the absorption of the vibration or oscillation and enhances the functionality of the vibratable element.

The second holding member may be substantially flexible, elastic and/or resilient. The second holding member may be configured to apply a resilient force, an elastic force and/or a spring force to the vibratable element, pressing of pushing the element against the first holding member. In this way, the vibratable element can be held in place, i.e., in its position relative to the housing, in a particularly reliable manner.

The second holding member may be made of a substantially flexible material, e.g., soft plastic or the like, such as a silicone, rubber, elastomer, thermoplastic elastomer (TPE), colour pigmentation, as well as a combination thereof, like blue thermoplastic elastomer (e.g. Thermolast K HTF 2147/17, blue) or the like.

The first and/or second holding member may be coated, caved and/or laminated with a further material or component even flexible or rigid, preferably with a relatively small thickness, so that it will not influence the functionality of the first and/or second holding member.

The first holding member may comprise a plurality of protrusions, e.g., ribs, ridges, base saddle, place restrictions, (stop) ridge or the like, in contact with the vibratable element. The vibratable element may be contacted by the first holding member only at or through the plurality of protrusions. By using a first holding member comprising a plurality of protrusions in contact with the vibratable element, the vibratable element can be securely and reliably held in its position relative to the housing while minimising the contact area between the element and the first holding member.

The protrusions, e.g., the ribs, ridges or the like, may be made from a substantially rigid material, such as hard plastic, glass fibre, metal, ceramic, a combination thereof or the like.

The protrusions may be coated, covered or encased with a substantially flexible material, e.g., a soft plastic, such as silicone, rubber, elastomer, thermoplastic elastomer (TPE), a combination thereof or the like.

The vibratable element may comprise a vibratable membrane. The vibratable membrane may be configured to generate an aerosol, i.e., to aerosolise or nebulise a fluid or liquid supplied to the membrane. In particular, the vibratable membrane may have a plurality of holes or openings. Fluid or liquid abutting the membrane on one side thereof may be conveyed through these holes or openings in the vibrating membrane to the other side thereof and emitted on this side as an aerosol.

The vibratable element may comprise a vibrator which is configured to vibrate the vibratable element. The vibrator may be configured to vibrate the vibratable membrane. The vibrator may comprise a piezoelectric element which is configured to vibrate or oscillate the vibratable element, e.g., the vibratable membrane or oscillatable assembly.

The vibrator may be attached, e.g., adhered, for example, using an adhesive, such as a glue, directly to the vibratable membrane or directly to a support member supporting the vibratable membrane. The support member may be formed integrally with the vibratable membrane.

The aerosol generator may be or form part of a nebuliser, such as a vibrating membrane nebuliser, e.g., an electronic vibrating membrane nebuliser, an atomiser or the like. In particular, the aerosol generator may be an electronic nebuliser, e.g., a piezoelectrically driven nebuliser, i.e., a nebuliser driven by a piezoelectric element. In this case, the piezoelectric element may form part of the vibrator and be arranged for vibrating or oscillating the vibratable element, e.g., the vibratable membrane or oscillatable assembly.

The housing may comprise a fluid or liquid reservoir for receiving a fluid or liquid to be aerosolised or nebulised.

The fluid or liquid reservoir may be arranged for directly receiving the fluid or liquid to be aerosolised. For example, the fluid or liquid reservoir may be configured as or have a fluid or liquid chamber or container into which a fluid or liquid can be directly filled.

Further, the fluid or liquid reservoir may be arranged for receiving a fluid or liquid containing vessel. In particular, the fluid or liquid reservoir may be designed so that it does not directly receive the fluid or liquid but rather has an opening element, such as a thorn, a spike, a hollow needle or the like, arranged on its inside that opens the fluid containing vessel, e.g., a vial, a blister, an ampoule, a container, a canister, a reservoir, a cartridge, a pot, a tank, a pen, a storage, a syringe or the like, inserted therein.

The fluid or liquid reservoir may be arranged in fluid communication with the vibratable element, e.g., the vibratable membrane. The fluid may be delivered via gravitational force to the vibratable element.

A fluid or liquid to be nebulised or aerosolised by the aerosol generator may be a fluid or liquid for the generation of a pharmaceutical aerosol for the delivery of an active compound.

An active compound is a natural, biotechnology-derived or synthetic compound or mixture of compounds useful for the diagnosis, prevention, management or treatment of a disease, condition or symptom of an animal, in particular a human.

Other terms which may be used as synonyms of active compounds include, for example, active ingredient, active pharmaceutical ingredient, drug substance, diagnostic material, drug, medicament and the like. The fluid could be of a liquid, solution, suspension, colloidal mixture or liposomal formulation form and can be prepared, mixed or opened before or during the application.

The active compound comprised in the fluid to be nebulised or aerosolised by the aerosol generator may be a drug substance or a medicament which is useful for the prevention, management, diagnosis or treatment of any disease, symptom or condition affecting the body cavities, the abdomen, the eyes, the intestine, the stomach, the nose, the sinuses, the osteomeatal complex, the mouth, the trachea, the lungs, the bronchia, the bronchioles, the alveoli and/or the respiratory tract.

Among the active compounds which may be useful for serving one of the purposes named previously and that may be used together with the present invention, are, for example, substances selected from the group consisting of anti-inflammatory compounds, anti-infective agents, antiseptics, prostaglandins, endothelin receptor agonists, phosphodiesterase inhibitors, beta-2-sympathicomimetics, decongestants, vasoconstrictors, anticholinergics, immunomodulators, mucolytics, anti-allergic drugs, antihistaminics, mast-cell stabilizing agents, tumor growth inhibitory agents, wound healing agents, local anaesthetics, antioxidants, oligonucleotides, peptides, proteins, vaccines, vitamins, plant extracts, cholinesterase inhibitors, vasoactive intestinal peptide, serotonin receptor antagonists, and heparins, glucocorticoids, anti-allergic drugs, antioxidants, vitamins, leucotriene antagonists, anti-infective agents, antibiotics, antifungals, antivirals, mucolytics, decongestants, antiseptics, cytostatics, immunomodulators, vaccines, wound healing agents, local anaesthetics, oligonucleotides, xanthin derived agents, peptides, proteins, surfactants and plant extracts. Such compound may be used in the form of a suspension, a solution, a colloidal formulation (i.e., liposomal), etc.

Examples of potentially useful anti-inflammatory compounds are glucocorticoids and non-steroidal anti-inflammatory agents such as betamethasone, beclomethasone, budesonide, ciclesonide, dexamethasone, desoxymethasone, fluocinolone acetonide, fluocinonide, flunisolide, fluticasone, icomethasone, rofleponide, triamcinolone acetonide, fluocortin butyl, hydrocortisone, hydroxycortisone-17-butyrate, prednicarbate, 6-methylprednisolone aceponate, mometasone furoate, dehydroepiandrosterone-sulfate (DHEAS), elastane, prostaglandin, leukotriene, bradykinin antagonists, non-steroidal anti-inflammatory drugs (NSAIDs), such as ibuprofen including any pharmaceutically acceptable salts, esters, isomers, stereoisomers, diastereomers, epimers, solvates or other hydrates, prodrugs, derivatives, or any other chemical or physical forms of active compounds comprising the respective active moieties.

Examples of anti-infective agents, whose class or therapeutic category is herein understood as comprising compounds which are effective against bacterial, fungal, and viral infections, i.e. encompassing the classes of antimicrobials, antibiotics, antifungals, antiseptics, and antivirals, are penicillins, including benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amiidine penicillins (mecillinam);

cephalosporins, including cefazolins (cefazolin, cefazedone); cefuroximes (cefuroxim, cefamandole, cefotiam), cefoxitins (cefoxitin, cefotetan, latamoxef, flomoxef), cefotaximes (cefotaxime, ceftriaxone, ceftizoxime, cefmenoxime), ceftazidimes (ceftazidime, cefpirome, cefepime), cefalexins (cefalexin, cefaclor, cefadroxil, cefradine, loracarbef, cefprozil), and cefiximes (cefixime, cefpodoxim proxetile, cefuroxime axetil, cefetamet pivoxil, cefotiam hexetil), loracarbef, cefepim, clavulanic acid/amoxicillin, Ceftobiprole;

synergists, including beta-lactamase inhibitors, such as clavulanic acid, sulbactam, and tazobactam;

carbapenems, including imipenem, cilastin, meropenem, doripenem, tebipenem, ertapenem, ritipenam, and biapenem;

monobactams, including aztreonam;

aminoglycosides, such as apramycin, gentamicin, amikacin, isepamicin, arbekacin, tobramycin, netilmicin, spectinomycin, streptomycin, capreomycin, neomycin, paromoycin, and kanamycin;

macrolides, including erythromycin, clarythromycin, roxithromycin, azithromycin, dithromycin, josamycin, spiramycin and telithromycin;

gyrase inhibitors or fluroquinolones, including ciprofloxacin, gatifloxacin, norfloxacin, ofloxacin, levofloxacin, perfloxacin, lomefloxacin, fleroxacin, garenoxacin, clinafloxacin, sitafloxacin, prulifloxacin, olamufloxacin, caderofloxacin, gemifloxacin, balofloxacin, trovafloxacin, and moxifloxacin;

tetracycline, including tetracyclin, oxytetracyclin, rolitetracyclin, minocyclin, doxycycline, tigecycline and aminocycline;

glycopeptides, including vancomycin, teicoplanin, ristocetin, avoparcin, oritavancin, ramoplanin, and peptide 4;

polypeptides, including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin;

sulfonamides, including sulfadiazine, sulfamethoxazole, sulfalene, co-trimoxazole, co-trimetrol, co-trimoxazine, and co-tetraxazine;

azoles, including clotrimazole, oxiconazole, miconazole, ketoconazole, itraconazole, fluconazole, metronidazole, tinidazole, bifonazol, ravuconazol, posaconazol, voriconazole, and ornidazole and other antifungals including flucytosin, griseofulvin, tolnaftal, naftifin, terbinafin, amorolfin, ciclopiroxolamin, echinocandins, such as micafungin, caspofungin, anidulafungin;

nitrofurans, including nitrofurantoin and nitrofuranzone;

polyenes, including amphotericin B, natamycin, nystatin, flucytosine;

other antibiotics, including tithromycin, lincomycin, clindamycin, oxazolidinones (linzezolids), ranbezolid, streptogramine A+B, pristinamycin A+B, Virginiamycin A+B, dalfopristin/quinupristin (Synercid), chloramphenicol, ethambutol, pyrazinamid, terizidon, dapson, prothionamid, fosfomycin, fucidinic acid, rifampicin, isoniazid, cycloserine, terizidone, ansamycin, lysostaphin, iclaprim, mirocin B17, clerocidin, filgrastim, and pentamidine;

antivirals, including aciclovir, ganciclovir, birivudin, valaciclovir, zidovudine, didanosin, thiacytidin, stavudin, lamivudin, zalcitabin, ribavirin, nevirapirin, delaviridin, trifluridin, ritonavir, saquinavir, indinavir, foscarnet, amantadin, podophyllotoxin, vidarabine, tromantadine, and proteinase inhibitors, siRNA based drugs;

antiseptics, including acridine derivatives, iodine-povidone, benzoates, rivanol, chlorhexidine, quarternary ammonium compounds, cetrimides, biphenylol, clorofene, taurolidine, and octenidine;

plant extracts or ingredients, such as plant extracts from chamomile, hamamelis, echinacea, calendula, thymian, bromelain, papain, pelargonium, pine trees, essential oils, myrtol, pinen, limonen, cineole, thymol, mental, camphor, tannin, alpha-hederin, bisabolol, lycopodin, vitapherole;

wound healing compounds including dexpantenol, allantoin, vitamins, hyaluronic acid, alpha-antitrypsin, enorganic and organic zinc salts/compounds, salts of bismuth and selen, silver (Ag) ions/compounds;

interferones (alpha, beta, gamma), tumor necrosis factors, cytokines, interleukines;

immunmodulators including methotrexat, azathioprine, cyclosporine, tacrolimus, sirolimus, rapamycin, mofetil, and mofetil-mycophenolate;

cytostatics and metastasis inhibitors;

alkylants, such as nimustine, melphanlane, carmustine, lomustine, cyclophosphamide, ifosfamide, trofosfamide, chlorambucil, busulfane, treosulfane, prednimustine, thiotepa;

antimetabolites, e.g. cytarabine, fluorouracil, methotrexate, mercaptopurine, tioguanine;

alkaloids, such as vinblastine, vincristine, vindesine;
antibiotics, such as alcarubicine, bleomycine, dactinomycine, daunorubicins, doxorubicins, epirubicine, idarubicine, mitomycine, plicamycine;
complexes of transition group elements (e.g. Ti, Zr, V, Nb, Ta, Mo, W, Pt) such as carboplatinum, cis-platinum and metallocene compounds such as titanocendichloride;
amsacrine, dacarbazine, estramustine, etoposide, beraprost, hydroxycarbamide, mitoxanthrone, procarbazine, temiposide;
paclitaxel, gefitinib, vandetanib, erlotinib, poly-ADP-ribose-polymerase (PRAP) enzyme inhibitors, banoxantrone, gemcitabine, pemetrexed, bevacizumab, ranibizumab.

Examples of potentially useful mucolytics are DNase (including dornase alpha), P2Y2-agonists (denufosol), drugs affecting chloride and sodium permeation, such as N-(3,5-Diamino-6-chloropyrazine-2-carbony)-N'-{4-[4-(2,3-dihydroxypropoxy)-phenyl]butyl}guanidine methanesulfonate (PARION 552-02), heparinoids, guaifenesin, acetylcysteine, carbocysteine, ambroxol, bromhexine, tyloxapol, lecithins, myrtol, surfactants, surfactant proteins, recombinant surfactant proteins and/or any other chemical or physical forms of active compounds comprising the respective active moieties.

Examples of potentially useful vasoconstrictors and decongestants which may be useful to reduce the swelling of the mucosa are phenylephrine, naphazoline, tramazoline, tetryzoline, oxymetazoline, fenoxazoline, xylometazoline, epinephrine, isoprenaline, hexoprenaline, and ephedrine.

Examples of potentially useful local anaesthetic agents include benzocaine, tetracaine, procaine, lidocaine and bupivacaine.

Examples of potentially useful antiallergic agents include the afore-mentioned glucocorticoids, cromolyn sodium, nedocromil, cetrizin, loratidin, montelukast, roflumilast, ziluton, omalizumab, heparinoids and other antihistamins, including azelastine, cetirizin, desloratadin, ebastin, fexofenadin, levocetirizin, loratadin.

Examples of potentially useful anticholinergic agents include ipratropium bromide, tiotropium bromide, oxitropium bromide, glycopyrrolate.

Examples of potentially useful beta-2-sympathicomimetic agents include salbutamol, fenoterol, formoterol, indacaterol, isoproterenol, metaproterenol, salmeterol, terbutaline, clenbuterol, isoetarine, pirbuterol, procaterol, ritodrine.

Examples of xanthine derived agents include theophylline, theobromine, caffeine.

Antisense oligonucleotides are short synthetic strands of DNA (or analogs) that are complimentary or antisense to a target sequence (DNA, RNA) designed to halt a biological event, such as transcription, translation or splicing. The resulting inhibition of gene expression makes oligonucleotides dependent on their composition useful for the treatment of many diseases and various compounds are currently clinically evaluated, such as ALN-RSV01 to treat the respiratory syncytical virus, AVE-7279 to treat asthma and allergies, TPI-ASM8 to treat allergic asthma, 1018-ISS to treat cancer.

Examples of potentially useful peptides and proteins include antibodies against toxins produced by microorganisms, antimicrobial peptides such as cecropins, defensins, thionins, and cathelicidins.

Examples of potentially applicable antibodies are immunoglobulins (e.g. Ig, IgG, IgE, IgM, IgA) and/or any other chemical or physical forms of active compounds comprising the respective active moieties thereof.

The second holding member may be provided on, e.g., attached or secured to, the fluid or liquid reservoir. In this way, the relative alignment or orientation between the vibratable element and the fluid reservoir can be established and maintained in a particularly precise and reliable manner. Hence, the flow of fluid or liquid from the fluid or liquid reservoir to the vibratable element can be accurately and reliably controlled, thus further enhancing aerosol quality and dosage accuracy.

The second holding member may be configured to guide the fluid or liquid from the fluid or liquid reservoir to the vibratable element, e.g., the vibratable membrane and/or vibratable head, e.g. via gravitational force. By using the same member for holding the vibratable element and guiding the fluid or liquid from the fluid or liquid reservoir to the element, the number of parts of the aerosol generator can be reduced. In this way, the assembly process can be simplified, the aerosol generator can be rendered more robust and stable and the manufacturing costs can be reduced. Moreover, the control of the flow of fluid or liquid from the fluid or liquid reservoir to the vibratable element can be further improved.

The vibratable element may comprise one or more electrical contacts, e.g., plugs, connectors, jacks, clips, cinches or the like, for connection to a control, e.g., an external control.

The control may be any type of control, e.g., a control unit, a control element, a control circuit or the like. The control may be capable of operating the vibrator of the aerosol generator. The control may be connectable through the one or more electrical contacts to the vibrator, e.g., to a power supply element of the vibrator.

The one or more electrical contacts may be formed from a metal sheet, such as a stainless steel sheet, e.g., punched out from the metal sheet. The one or more electrical contacts may be bent, e.g., after punching them out, for example, bent into a curved and/or cambered shape. The vibratable element may comprise a plurality of electrical contacts for connection to the control and all of the plurality of electrical contacts may have the same configuration.

The one or more electrical contacts may be connected to the remainder of the vibratable element, e.g., to a front portion thereof and/or the vibrator, through a strip conductor, e.g., a flexible strip conductor, such as a printed circuit board track or a strip line. The strip conductor may have contact pads, e.g., gold contact pads, for connection with the one or more electrical contacts and/or the remainder of the vibratable element.

The one or more electrical contacts and/or the remainder of the vibratable element may be secured to and/or electrically connected with the contact pads of the strip conductor by brazing, soldering, welding, resistance welding, HF resistance welding, electrically conductive coating, electrically conductive gluing or the like.

A portion of the vibratable element comprising one or more or all of the contacting areas, in which the one or more electrical contacts and/or the remainder of the vibratable element are connected, e.g. welded, to the strip conductor, may be covered or encapsulated with a cover member. The cover member may electrically insulate the one or more contacting areas. The cover member may be made of a plastic and/or insulating material. The cover member may be applied to the one or more contacting areas, for example, by injection moulding or a hot-melting adhesive process.

Further, the invention provides an aerosol delivery device comprising the aerosol generator.

The aerosol delivery device may be an aerosol generation device, an aerosol inhalation device, a medical aerosol device, an aerosol diagnostic device, an aerosol prophylactic device, an aerosol therapeutic device, an aerosol humidification device, an aerosol therapy device or the like. The aerosol delivery device may comprise a control as defined above. The aerosol delivery device may comprise an aerosol cavity or an aerosol chamber for receiving an aerosol generated by the aerosol generator. The aerosol delivery device may comprise a mouthpiece and/or a nosepiece and/or nasal prongs and/or an endotracheal tube and/or a ventilator tube system and/or a face mask. The generated aerosol may be supplied from the aerosol cavity or chamber to a user or patient through the mouthpiece and/or nosepiece and/or nasal prongs and/or endotracheal tube and/or ventilator tube system and/or face mask.

Moreover, the present disclosure provides a fluid or liquid reservoir for an aerosol generator or an aerosol delivery device, the fluid or liquid reservoir comprising a fluid or liquid chamber for receiving a fluid or liquid to be aerosolised or nebulised. The fluid or liquid chamber comprises an opening for guiding the fluid or liquid outside the fluid or liquid chamber, e.g., to a vibratable element, a vibratable head, a vibratable membrane, or an oscillatable assembly of an aerosol generator. The fluid or liquid chamber, in particular, the opening, may include a flexible component and/or flexible material, such as a seal, sealing lip, sealing ring, lip seal, joint ring, or seal gasket.

The aerosol delivery device may comprise an aerosol generator with a vibratable element, e.g., the aerosol generator defined above, wherein the vibratable element may be arranged in horizontal alignment or orientation, i.e., so that the vibratable element lies in the horizontal plane when the fluid or liquid reservoir is in the upright, i.e., vertical position.

BRIEF DESCRIPTION OF THE DRAWINGS

Hereinafter, non-limiting examples of the invention are explained with reference to the drawings, in which.

DETAILED DESCRIPTION OF CURRENTLY PREFERRED EMBODIMENTS

Figure 1:
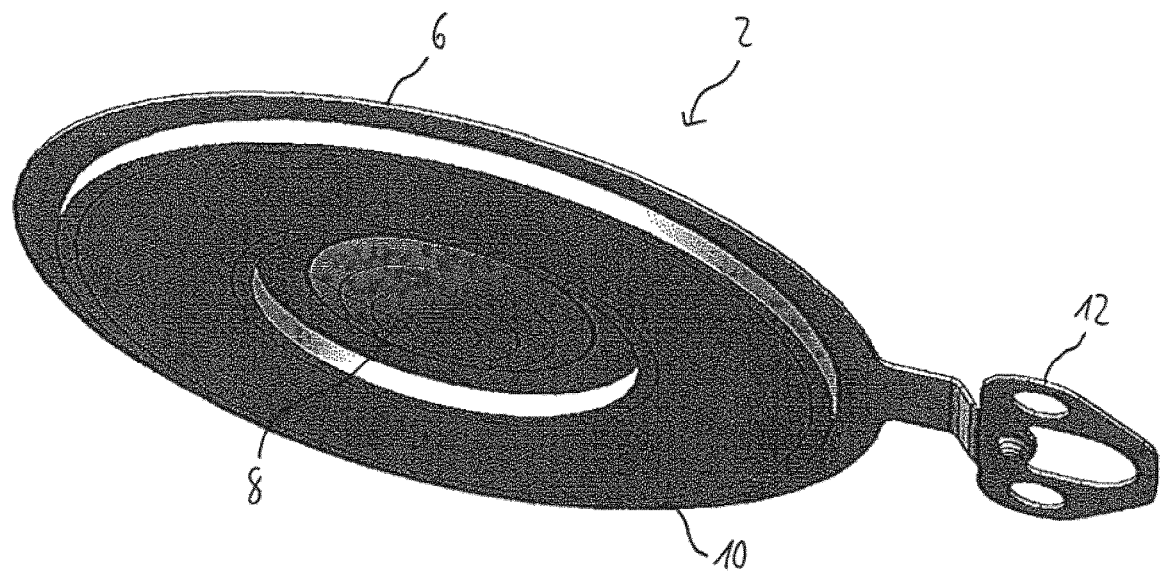
FIG. 1 shows a schematic perspective bottom view of a portion of a vibratable element of an aerosol generator according to an embodiment of the present invention.

FIG. 1 shows a schematic perspective bottom view of a front portion 2 of a vibratable element 4 (see FIG. 2) of an aerosol generator 1 (see FIG. 9) according to a currently preferred embodiment of the present invention.

The front portion 2 of the vibratable element 4 comprises a support member 6, a vibratable membrane 8 with a plurality of openings or holes (not shown), an annular piezoelement 10 and a connection portion 12. The vibratable membrane 8 is integrally formed with the support member 6. The vibratable membrane 8 and the support member 6 are made from a metal, such as stainless steel.

The piezoelement 10 is attached, e.g., adhered, for example, using an adhesive, such as a glue, directly to the support member 6. The piezoelement 10 serves as a vibrator for vibrating the vibratable membrane 8.

Figure 2:
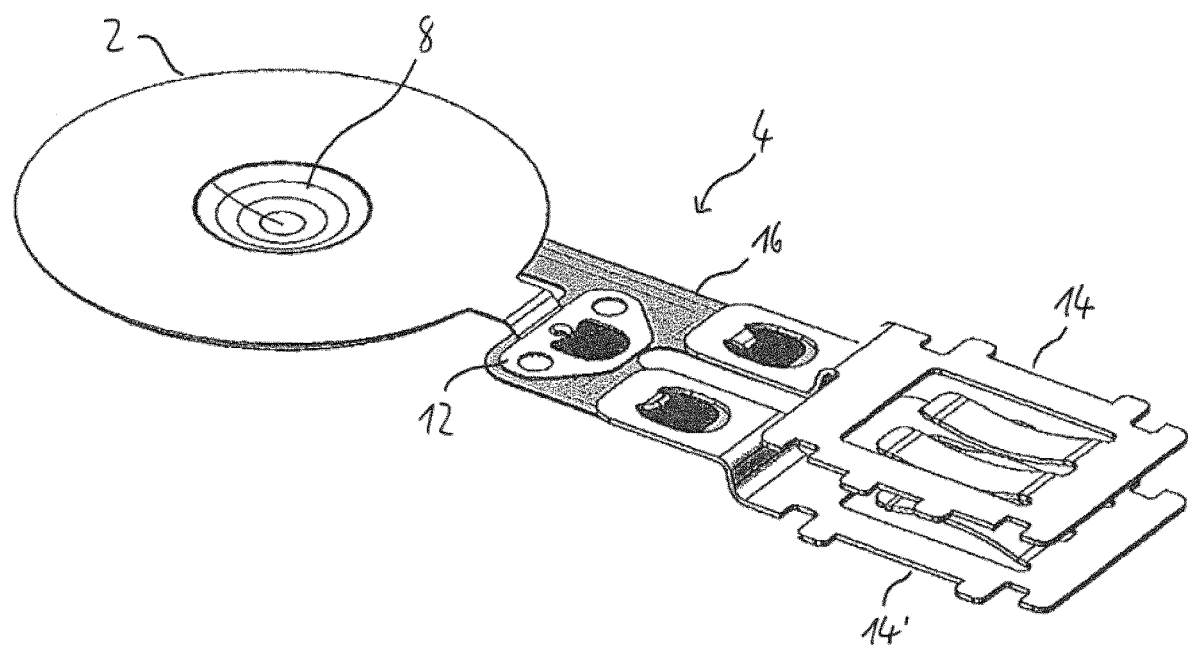
FIG. 2 shows a schematic perspective top view of the vibratable element of the aerosol generator according to the embodiment of the present invention.

As is shown in FIG. 2, the vibratable element 4 further comprises a pair of electrical contacts 14, 14', e.g., plugs, for connection to a control (not shown). The electrical contacts 14, 14' are punched out from a stainless steel sheet and subsequently bent, i.e., bent into the shape shown in FIG. 2. Both electrical contacts 14, 14' may have the same configuration, but the first contact 14 is rotated by 180° around its longitudinal axis relative to the second contact 14'.

The electrical contacts 14, 14' are connected to the connection member 12 and the piezoelement 10 through a flexible strip conductor 16, such as a printed circuit board track or a strip line. The flexible strip conductor 16 has gold contact pads for connection with the electrical contacts 14, 14' and the connection member 12. The electrical contacts 14, 14' and the connection member 12 are secured to and electrically connected with the respective gold contact pads of the strip conductor 16 by welding, especially by resistance stud welding.

Figure 3:
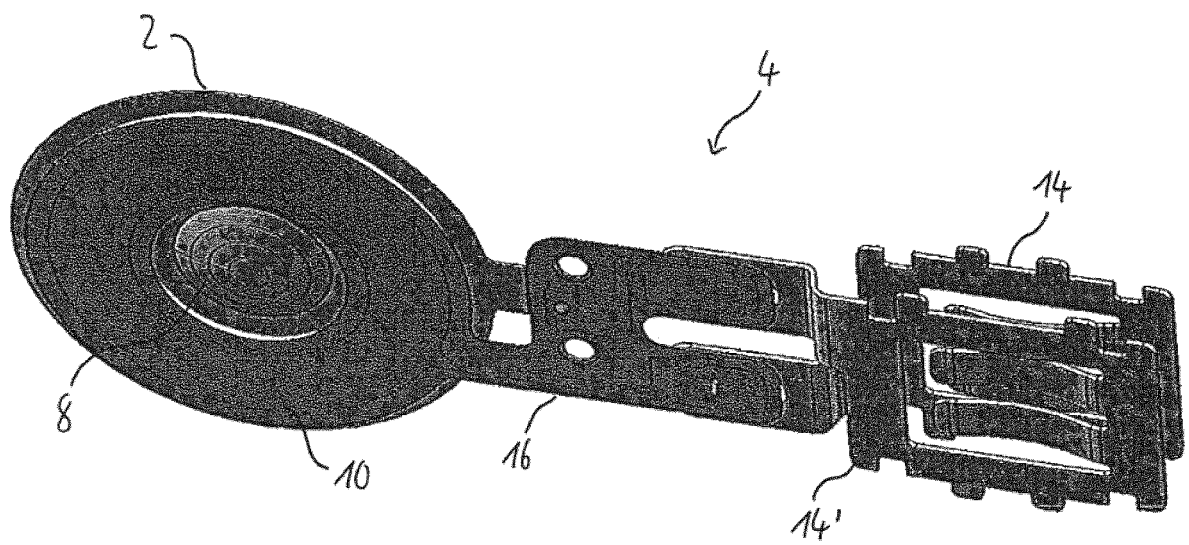
FIG. 3 shows a schematic perspective bottom view of the vibratable element of the aerosol generator according to the embodiment of the present invention.
Figure 4:
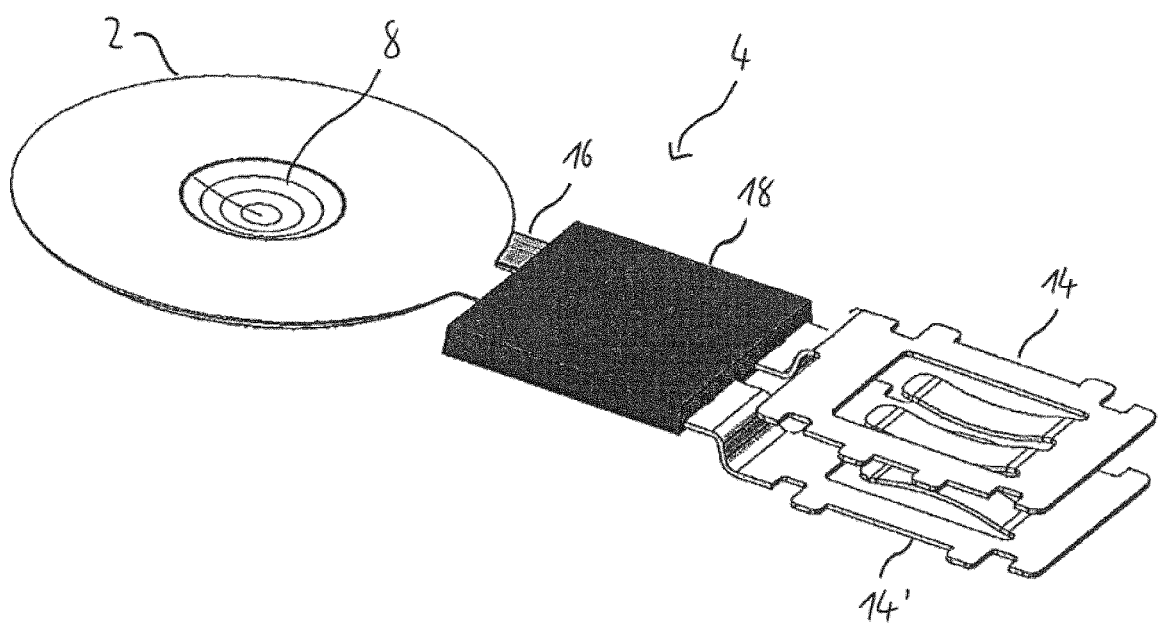
FIG. 4 shows a schematic perspective top view of the vibratable element of the aerosol generator according to the embodiment of the present invention with a cover element.
Figure 5:
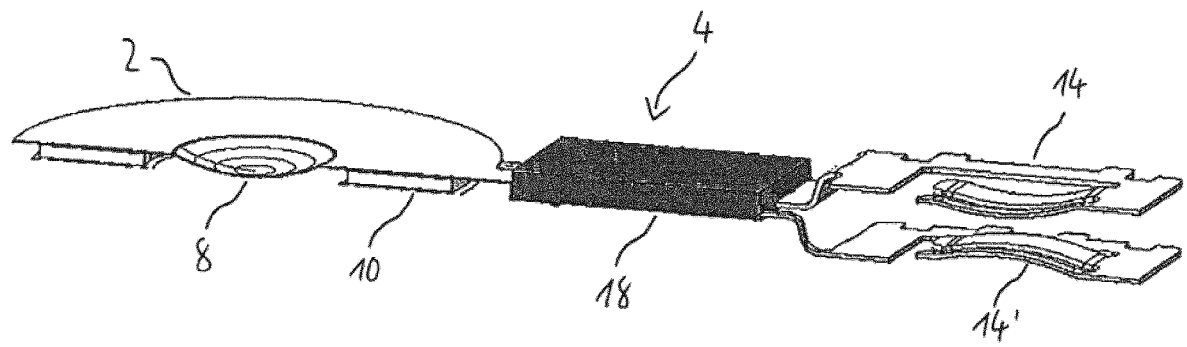
FIG. 5 shows a schematic longitudinally cut cross-sectional view of the vibratable element shown in FIG. 4.

Further, the strip conductor 16 is secured to and electrically connected with the piezoelement 10, as is shown in FIG. 3. The portion of the vibratable element 4 comprising the contacting or welding areas where the connection member 12 and the two electrical contacts 14, 14' are welded to the strip conductor 16 is encapsulated with a cover member 18, as is shown in FIGS. 4 and 5, and thus electrically insulated. The cover member 18 is made of a plastic material.

In the above-described manner, the vibratable element 4 can be manufactured in a simple, reliable and cost efficient way, using a minimum amount of parts.

Figure 9:
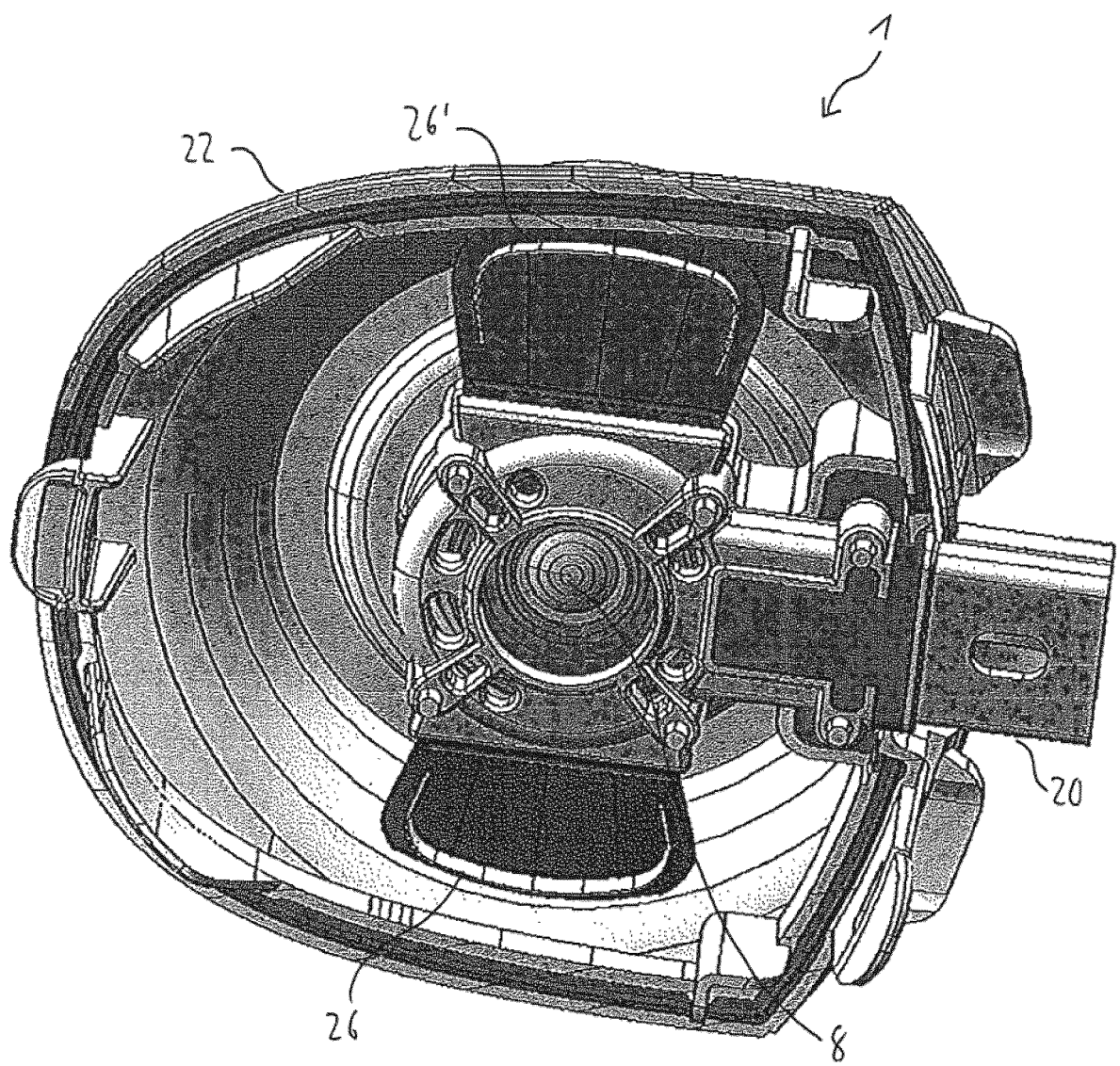
FIG. 9 shows a schematic perspective bottom view of the part of the housing shown in FIG. 7 with a fluid reservoir attached thereto.
Figure 10:
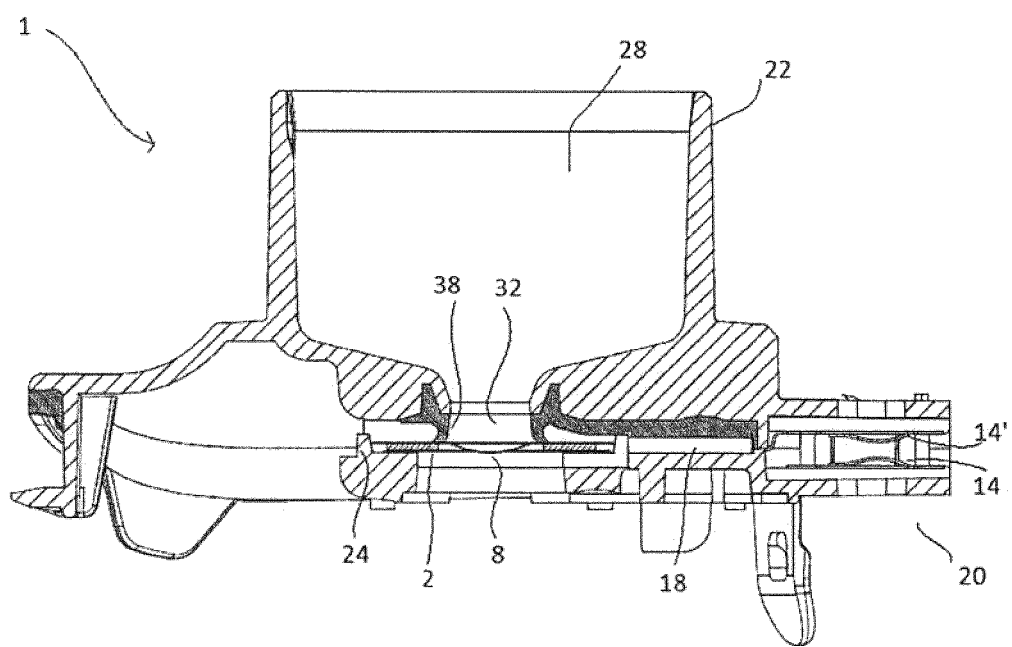
FIG. 10 shows a schematic longitudinally cut cross-sectional view of the part of the housing shown in FIG. 9.

The aerosol generator 1 of the currently preferred embodiment further comprises a housing having a lower housing part 20 (see FIG. 6) and a fluid reservoir 22 (see FIGS. 9 and 10).

Figure 6:
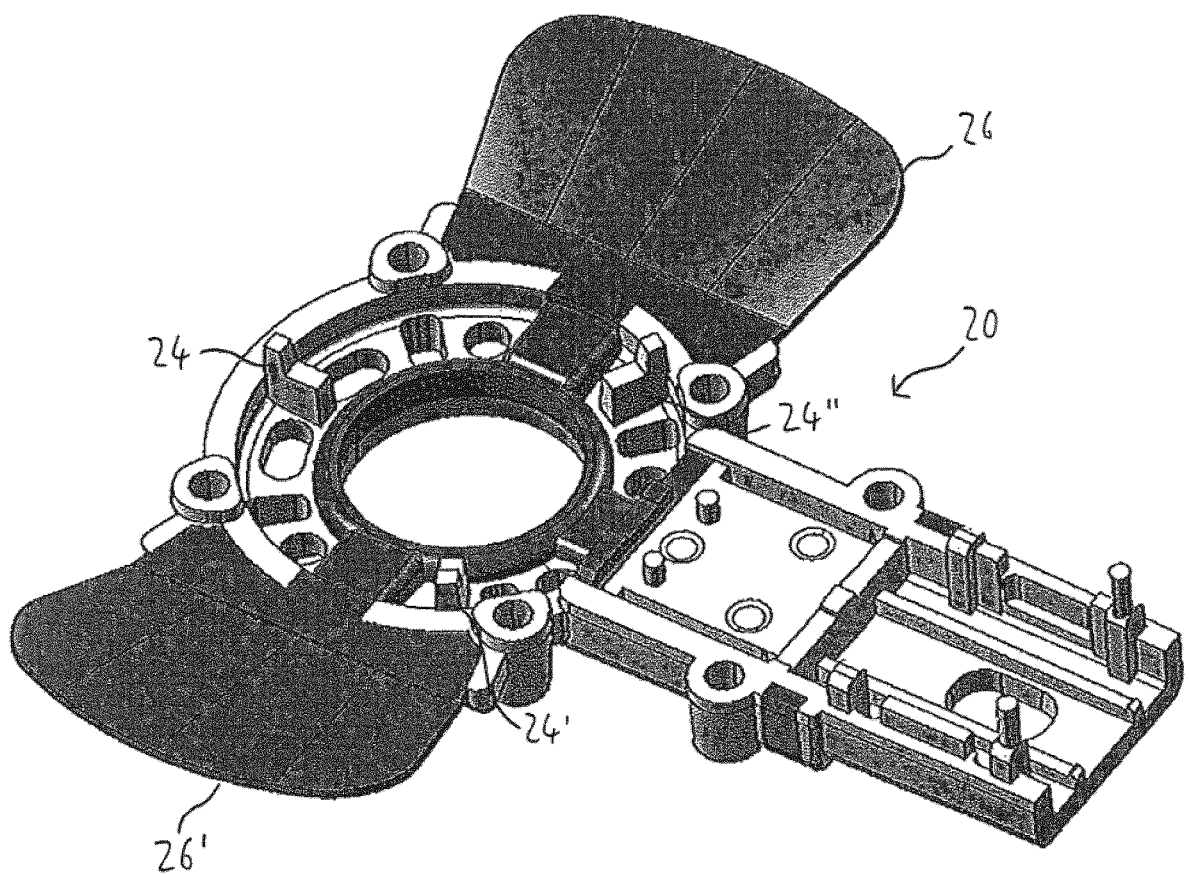
FIG. 6 shows a schematic perspective top view of a lower part of a housing of the aerosol generator according to the embodiment of the present invention.

As is shown in FIG. 6, the lower housing part 20 comprises three protrusions 24, 24', 24", i.e., ribs, for supporting and holding the front portion 2 of the vibratable element 4. The protrusions 24, 24', 24" are made from a rigid material, such as hard plastic, metal, ceramic or the like. The protrusions 24, 24', 24" have a stepped upper surface, supporting the front portion 2 of the vibratable element 4 in orthogonal directions, namely in the axial direction, i.e., from below, and in the radial direction thereof. The three protrusions 24, 24', 24" form the first holding member of the housing of the aerosol generator 1.

The lower housing part 20 further comprises a pair of valve flaps 26, 26'. The valve flaps 26, 26' are hingedly attached to the remainder of the lower housing part 20 so as to allow pivoting thereof towards and away from the protrusions 24, 24', 24". During an inhalation manoeuvre of a user or patient, the valve flaps 26, 26' open, so as to allow ambient air to flow into the aerosol generator 1. In this way, an aerosol generated by the aerosol generator 1 can be supplied to the user or patient together with the ambient air introduced via a direct flow path into the generator 1. However, during exhalation by the user or patient, the valve flaps 26, 26' close, thus reliably avoiding any undesired transport of aerosol outside the aerosol generator 1. Hence, any loss of aerosol can be reliably prevented.

The lower housing part 20 may be formed by moulding, for example, by injection moulding. In one embodiment, the protrusions 24, 24', 24" may be coated, covered or encased with a flexible material, e.g., a soft plastic, such as a thermoplastic elastomer.

Figure 7:
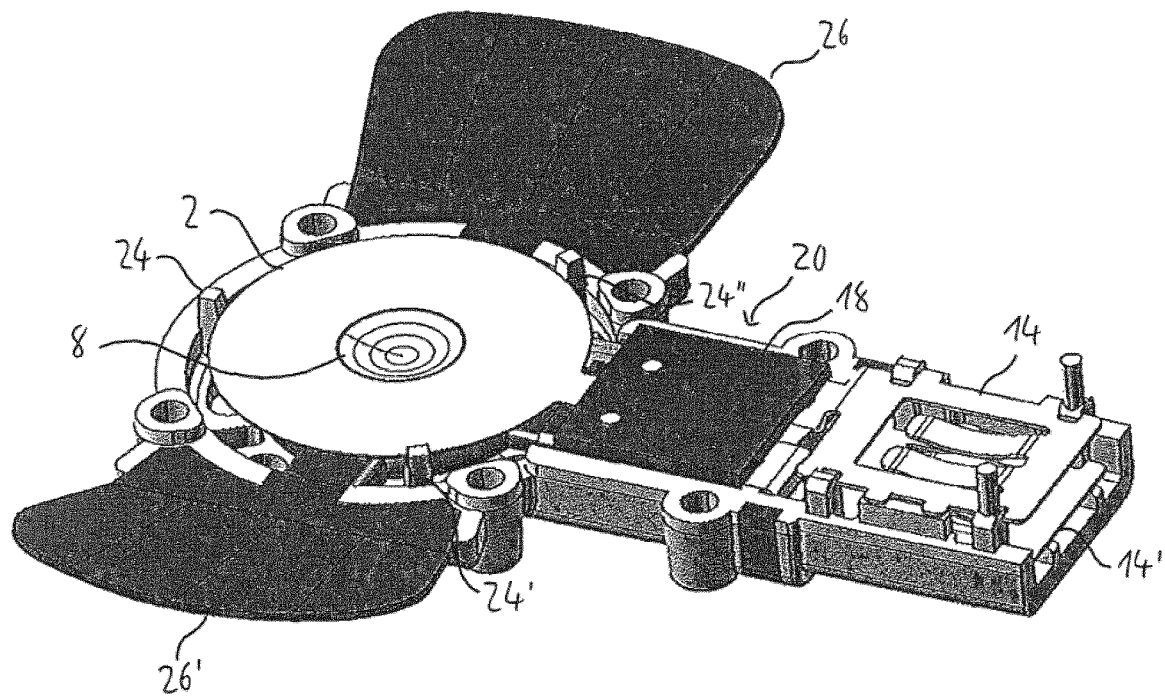
FIG. 7 shows a schematic perspective top view of the part of the housing shown in FIG. 6 with the vibratable element shown in FIG. 4 inserted therein.
Figure 8:
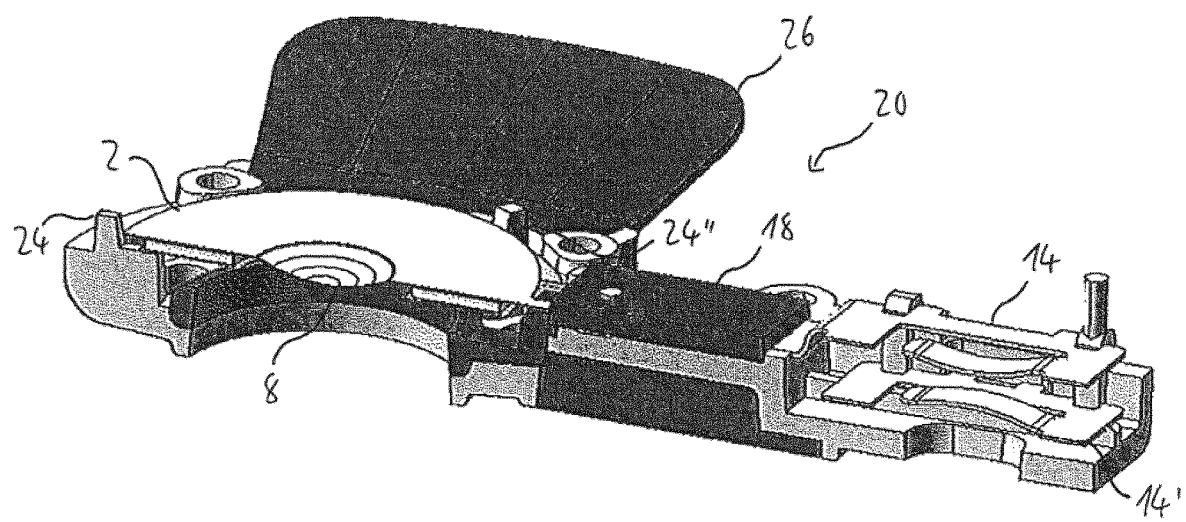
FIG. 8 shows a schematic longitudinally cut cross-sectional view of the part of the housing shown in FIG. 7.

The vibratable element 4 is received in the lower housing part 20 with the front portion 2 resting on the protrusions 24, 24', 24", as is shown in FIGS. 7 and 8. As can be seen from these figures, the protrusions 24, 24', 24" inhibit any movement of the front portion 2 of the vibratable element 4 in radial and downward axial directions.

In particular, when assembling the aerosol generator 1, the front portion 2 of the vibratable element 4 is first placed on the rigid protrusions 24, 24', 24", These protrusions 24, 24', 24" provide stable support to the front portion 2, reliably preventing any undesired movement thereof, both in the further assembly process and during operation of the aerosol generator 1.

The housing of the aerosol generator 1 further comprises the fluid reservoir 22, as is shown in FIGS. 9 and 10. The fluid reservoir 22 is placed on top of the lower housing part 20, thereby completing the housing of the aerosol generator 1. The fluid reservoir 22 may be formed by moulding, for example, by injection moulding.

The housing and the vibratable element 4 together form the aerosol generator 1.

The fluid reservoir 22 comprises a fluid chamber 28 for receiving a fluid (not shown) to be aerosolised. The fluid chamber 28 comprises an opening 32 for guiding the fluid outside the fluid chamber 28, i.e., towards the vibratable membrane 8. The fluid reservoir 22 is arranged so that its axial direction is substantially perpendicular to the plane of the front portion 2 of the vibratable element 4.

The fluid reservoir 22 further comprises a sealing member 38 which is secured to the fluid reservoir 22 in a position below the opening 32 of the fluid chamber 28 (see FIG. 10). The sealing member 38 is made of a flexible, elastic and resilient material, e.g., a soft plastic, such as a thermoplastic elastomer, silicone, rubber, o-ring seal or the like.

The sealing member 38 is configured to guide the fluid from the opening 32 of the fluid chamber 28 of the fluid reservoir 22 to the vibratable membrane 8 of the vibratable element 4 by gravitational force.

When the fluid reservoir 22 is placed on top of the lower housing part 20, the sealing member 38 contacts the upper surface of the front portion 2 of the vibratable element 4. The sealing member 38 of the fluid reservoir 22 thus forms the second holding member of the housing.

The resilient force of the sealing member 38 presses the front portion 2 of the vibratable element 4 against the protrusions 24, 24', 24" of the lower housing part 20. The front portion 2 is thus securely held between the protrusions 24, 24', 24" and the sealing member 38 in the axial and radial directions. Any undesired movement of the vibratable element 4 during assembly and operation of the aerosol generator 1 is thus reliably prevented.

In the following, an example of the operation of the aerosol generator 1 will be explained.

A predetermined amount of fluid, e.g., a liquid, is filled into the fluid chamber 28 of the fluid reservoir 22, Subsequently, the upper portion of the fluid chamber 28 is closed, for example, with a cap, such as a screw cap (not shown). A portion of the fluid flows through the opening 32 of the fluid chamber 28 and the sealing member 38, so as to abut the vibratable membrane 8 of the vibratable element 4. An activation signal of the control (not shown) is supplied to the piezoelement 10 of the front portion 2 of the vibratable element 4 via the electrical contacts 14, 14' and the strip conductor 16, causing the membrane 8 to vibrate.

The fluid abutting the membrane 18 is conveyed through the holes or openings (not shown) in the vibrating membrane 8 and thereby aerosolised into an aerosol cavity or chamber (not shown) of an aerosol delivery device (not shown) arranged below the vibrating membrane 8. The aerosol thus provided in the aerosol cavity or chamber can be inhaled by a user or patient through a mouthpiece, nosepiece, nasal prongs, endotracheal tube, ventilator tube system, and/or face mask (not shown) of the aerosol delivery device.

In order to supply a sufficient amount of air, the valve flaps 26, 26' of the lower housing part 20 open during an inhalation manoeuvre of the user or patient, so as to allow ambient air to flow via a flow path directly into the aerosol delivery device. In this way, the aerosol generated by the aerosol generator 1 is supplied to the user or patient together with the air introduced by the valve flaps 26, 26'. During exhalation by the user or patient, the valve flaps 26, 26' close, thus reliably avoiding any undesired transport of the generated aerosol outside the aerosol delivery device. Therefore, any loss of aerosol can be reliably prevented.

The foregoing embodiments and their variants have been disclosed for illustrative purposes only, and further variation is wholly possible within the capabilities of the skilled reader. Accordingly, the appended claims are intended to cover all modifications, substitutions, alterations, omissions and additions which one skilled in the art could achieve from the foregoing disclosure, taking into account his own general and specialist knowledge and expertise.

The invention claimed is:

1. An aerosol generator, comprising:
    a housing having a first holding member and a second holding member,
    a vibratable element for generating an aerosol, and
    a vibrator which is configured to vibrate the vibratable element,
    wherein
    the vibratable element is at least partially accommodated in the housing,
    the vibratable element is contacted by and held between the first and second holding members, and
    the first holding member is less flexible than the second holding member,
    wherein
    the first holding member comprises a plurality of protrusions in contact with the vibratable element,
    wherein
    the housing comprises a fluid reservoir for receiving a fluid to be aerosolised, and
    wherein
    the second holding member is arranged on a side of the vibratable element which faces the fluid reservoir,
    wherein
    the vibrator is attached directly to the vibratable element, wherein
the vibratable element comprises a vibratable membrane,
wherein
the vibratable membrane has a plurality of holes or openings, and
wherein
the aerosol generator is configured so that the fluid is conveyed through the holes or openings of the vibratable membrane and thereby aerosolised.

2. The aerosol generator according to claim 1, wherein the first holding member is substantially rigid.

3. The aerosol generator according to claim 1, wherein the second holding member is substantially flexible.

4. The aerosol generator according to claim 1, wherein the protrusions are made from a substantially rigid material.

5. The aerosol generator according to claim 1, wherein the second holding member is provided on the fluid reservoir.

6. The aerosol generator according to claim 1, wherein the second holding member is configured to guide the fluid from the fluid reservoir to the vibratable element.

7. The aerosol generator according to claim 1, wherein the vibratable element comprises one or more electrical contacts for connection to a control.

8. An aerosol delivery device comprising the aerosol generator according to claim 1.

9. An aerosol generator, comprising:
a housing having a first holding member and a second holding member,
a vibratable element for generating an aerosol, and
a vibrator which is configured to vibrate the vibratable element,
wherein
the vibratable element is at least partially accommodated in the housing,
the vibratable element is contacted by and held between the first and second holding members, and
the first holding member is less flexible than the second holding member,
wherein
the first holding member comprises a plurality of protrusions in contact with the vibratable element,
wherein
the housing comprises a fluid reservoir for receiving a fluid to be aerosolised,
wherein
the vibrator is attached directly to the vibratable element,
wherein
the vibratable element comprises a vibratable membrane,
wherein
the vibratable membrane has a plurality of holes or openings, and
wherein
the aerosol generator is configured so that the fluid is conveyed through the holes or openings of the vibratable membrane and thereby aerosolised.

* * * * *